(12) United States Patent
Altmann et al.

(10) Patent No.: US 11,583,332 B2
(45) Date of Patent: Feb. 21, 2023

(54) COMBINED CARDIAC PACING AND IRREVERSIBLE ELECTROPORATION (IRE) TREATMENT

(71) Applicant: BIOSENSE WEBSTER (ISRAEL) LTD., Yokneam (IL)

(72) Inventors: Andres Claudio Altmann, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 288 days.

(21) Appl. No.: 16/726,301

(22) Filed: Dec. 24, 2019

(65) Prior Publication Data

US 2021/0186593 A1 Jun. 24, 2021

(51) Int. Cl.
*A61B 18/12* (2006.01)
*A61N 1/32* (2006.01)
*A61B 18/00* (2006.01)

(52) U.S. Cl.
CPC .......... *A61B 18/1233* (2013.01); *A61N 1/327* (2013.01); *A61B 2018/00577* (2013.01); *A61B 2018/00613* (2013.01); *A61B 2018/00702* (2013.01)

(58) Field of Classification Search
CPC ...... A61B 18/1233; A61B 2018/00577; A61B 2018/00613; A61B 2018/00702; A61B 2018/00351; A61B 2018/00732; A61B 18/1492; A61B 18/12; A61N 1/327
See application file for complete search history.

(56) References Cited

U.S. PATENT DOCUMENTS

| 8,048,067 B2 | 11/2011 | Davalos |
| 8,221,411 B2 | 7/2012 | Francischelli |
| 9,987,081 B1 | 6/2018 | Bowers |
| 10,271,893 B2 | 4/2019 | Stewart |
| 10,342,598 B2 | 7/2019 | Long |
| 10,531,914 B2 | 1/2020 | Stewart |
| 2016/0051324 A1 | 2/2016 | Stewart |

(Continued)

FOREIGN PATENT DOCUMENTS

| EP | 2130507 A1 | 12/2009 | |
| WO | WO-9518649 A1 * | 7/1995 | ............. A61N 1/306 |
| WO | WO2011159641 A1 | 12/2011 | |

(Continued)

OTHER PUBLICATIONS

European Search Report for corresponding EPA No. 20216796.1 dated May 14, 2021.

*Primary Examiner* — Thomas A Giuliani
*Assistant Examiner* — Christine A Dedoulis
(74) *Attorney, Agent, or Firm* — Dergosits & Noah LLP; Todd A. Noah

(57) ABSTRACT

A cardiac pacing and irreversible electroporation (IRE) apparatus includes a pulse generator and a shaping circuit. The pulse generator is configured to generate IRE pulses of prespecified shape and repetition rate. The shaping circuit is configured to convert some of the IRE pulses into pacing pulses of prespecified frequency and amplitude, to generate an output signal including ones of the IRE pulses interleaved with ones of the pacing pulses, and to output the output signal to a probe in a heart of a patient for applying the output signal to cardiac tissue.

12 Claims, 2 Drawing Sheets

(56) References Cited

U.S. PATENT DOCUMENTS

2016/0166310 A1* 6/2016 Stewart .............. A61B 18/1492
606/34
2018/0042674 A1 2/2018 Mickelsen

FOREIGN PATENT DOCUMENTS

WO    WO-2017024123 A1 * 2/2017 ......... A61B 18/1206
WO    WO2017024123 A1    2/2017

* cited by examiner

COMBINED CARDIAC PACING AND IRREVERSIBLE ELECTROPORATION (IRE) TREATMENT

FIELD OF THE INVENTION

The present invention relates generally to electroanatomical mapping combined with ablation, and particularly to cardiac pacing and irreversible electroporation (IRE).

BACKGROUND OF THE INVENTION

Pacing cardiac tissue to identify a source of arrhythmia, followed with ablating the tissue was previously proposed in the patent literature. For example, U.S. Pat. No. 9,987,081 describes systems, devices, and methods for electroporation ablation therapy, with the system including a pulse waveform signal generator for medical ablation therapy that may be coupled to an ablation device including at least one electrode for ablation pulse delivery to tissue. The signal generator may generate and deliver voltage pulses to the ablation device in the form of a pulse waveform in a predetermined sequence. In some embodiments, the system may include a cardiac stimulator configured to generate a pacing signal for cardiac stimulation during use. The cardiac stimulator may be communicably coupled to the signal generator and further configured to transmit an indication of the pacing signal to the signal generator. The processor of the signal generator may be further configured to generate the pulse waveform in synchronization with the indication of the pacing signal, where the synchronization may include a predetermined offset. In other embodiments, a method of treatment may include electrically pacing the heart with a cardiac stimulator to ensure pacing capture to establish periodicity and predictability of the cardiac cycle, and then defining a time window within the refractory period of the cardiac cycle within which one or more pulsed ablation waveforms may be delivered.

As another example, U.S. Patent Application Publication 2018/0042674 describes a method including selecting a sub-set of electrode pairs of a multi-electrode catheter, the multi-electrode catheter configured to be disposed about a portion of a heart. A pacing signal is conveyed to a pacing lead configured to be operatively coupled to the heart. An electrocardiograph signal associated with a function of the heart is received at a feedback module of the electrode controller. In an embodiment, during a time window associated with at least one of the pacing signal or the electrocardiograph signal, a pulsed voltage waveform is delivered to the sub-set of electrode pairs according to a sequential pattern, the pulsed voltage waveform including a pre-polarizing pulse followed by a polarizing pulse, the pre-polarizing pulse being generated by utilizing voltage spikes generated from switching on a discharge of a capacitor bank.

SUMMARY OF THE INVENTION

An exemplary embodiment of the present invention provides a cardiac pacing and irreversible electroporation (IRE) apparatus including a pulse generator and a shaping circuit. The pulse generator is configured to generate IRE pulses of prespecified shape and repetition rate. The shaping circuit is configured to convert some of the IRE pulses into pacing pulses of prespecified frequency and amplitude, to generate an output signal comprising ones of the IRE pulses interleaved with ones of the pacing pulses, and to output the output signal to a probe in a heart of a patient for applying the output signal to cardiac tissue.

In some exemplary embodiments, the apparatus further includes a processor configured to (a) specify the shape and the repetition rate of the IRE pulses, (b) specify the frequency and the amplitude of the pacing pulses, and (c) specify the interleaved output signal, by specifying a number of the one or more IRE pulses and a number of the one or more pacing pulses.

In some exemplary embodiments, the shaping circuit is further configured to modify a prespecified shape of the IRE pulses.

In an exemplary embodiment, the shaping circuit is configured to interleave the IRE pulses with the pacing pulses in accordance with a configurable protocol.

There is additionally provided, in accordance with another exemplary embodiment of the present invention, a method of applying cardiac pacing and irreversible electroporation (IRE) pulses, the method including generating IRE pulses of prespecified shape and repetition rate. Some of the IRE pulses are converted into pacing pulses of prespecified frequency and amplitude, to generate an output signal including ones of the IRE pulses interleaved with ones of the pacing pulses. The output signal is outputted to a probe in a heart of a patient for applying the output signal to cardiac tissue.

In some exemplary embodiments, the method of applying further includes, using a processor, specifying the shape and the repetition rate of the IRE pulses. The frequency and the amplitude of the pacing pulses are specified. The interleaved output signal is specified by specifying a number of the one or more IRE pulses and a number of the one or more periods of the RF signal.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
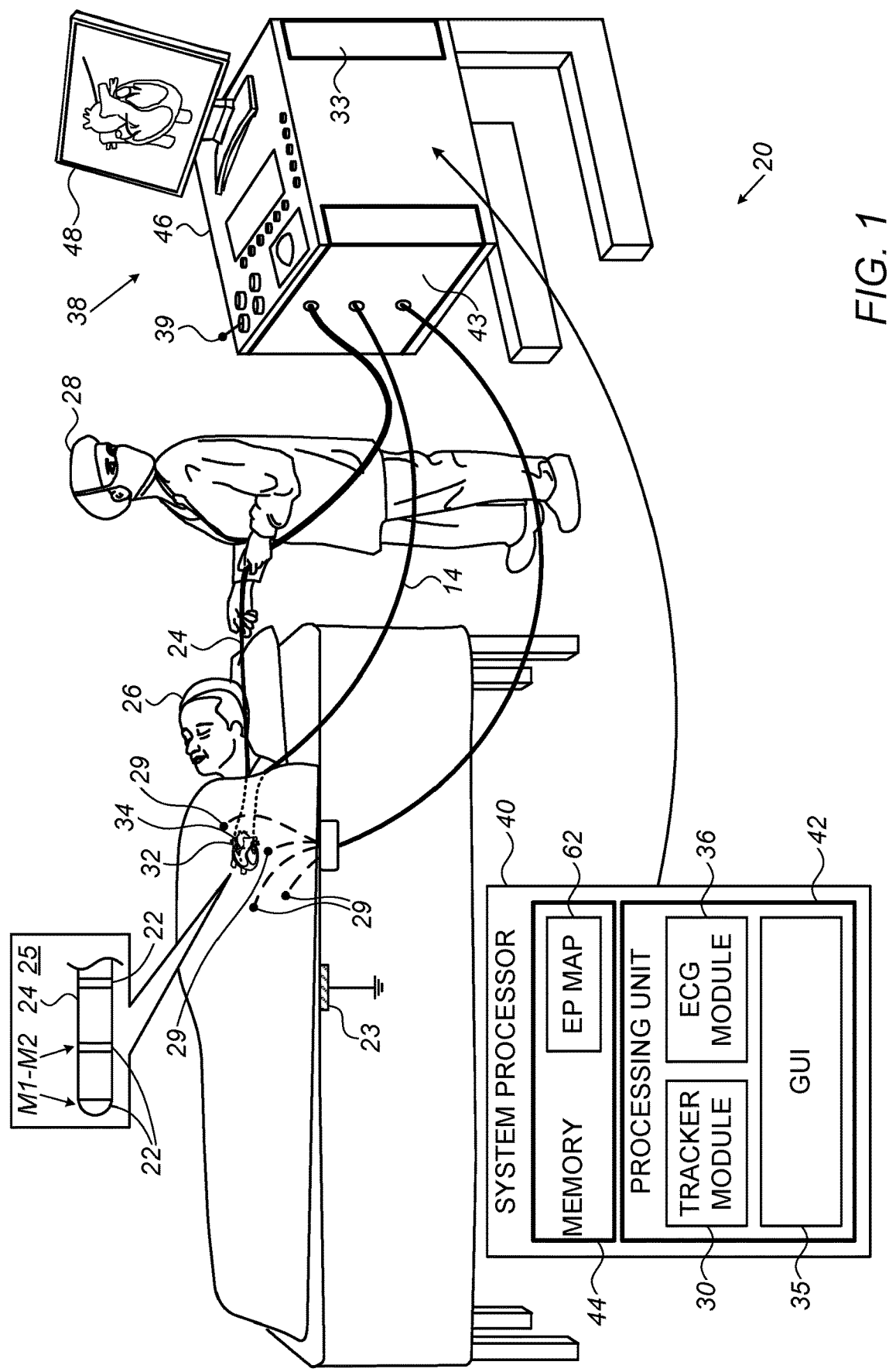
FIG. 1 is a schematic, pictorial illustration of combined cardiac pacing and irreversible electroporation (IRE) system, in accordance with an exemplary embodiment of the present invention.

Cardiac arrhythmia, which is defined as a variation from the normal heart sinus rhythm, may originate in, or be conducted by, different portions of cardiac tissue, named hereinafter "arrhythmogenic locations." One possible method to search for an arrhythmogenic location is to electrically stimulate selected locations on the cardiac tissue surface of a patient using bipolar electrical signals. Such stimulation, which may be done using an electrode pair on a catheter, may induce an electrocardiogram (ECG) signal pattern that meets one or more criteria to identify a stimulated location as an arrhythmogenic focus or pathway. The invasive diagnostic procedure described above is called "pacing."

A treatment of the identified arrhythmogenic location is done, for example, by irreversibly electroporating (IRE) the location, which generates a high electric field that kills targeted tissue cells, which is likely to reduce or eliminate the arrhythmia in question. However, it may be hard to pace and subsequently apply IRE treatment at the same location exactly, in part due to cardiac motion. Moreover, even if maintaining a same location during pacing and subsequent IRE treatment is sufficiently achieved, e.g., using a single catheter for both procedures, two different sets of driving electronics (e.g., generators) are still required because of the different voltage requirements.

Exemplary embodiments of the present invention that are described hereinafter provide a combined technique to perform substantially simultaneously and/or sequentially diagnostic pacing and IRE treatment of arrhythmia at a given cardiac tissue location using combined generation and application of cardiac pacing pulses and of IRE pulses. While the high-voltage requirements for IRE may be in the range of kilovolts, the power requirements for IRE are small, in a range of a few tens of milliwatts. Thus, much of the circuitry for both the IRE pulse generation and for the pacing may be the same, the only differences being the pulse sequencing and amplitude.

In the disclosed technique, sequences of pacing pulses and IRE pulses are applied to the same tissue location at substantially the same time by interleaving one or more pacing pulses with one or more IRE pulses. In some exemplary embodiments, a cardiac pacing and IRE treatment apparatus is provided, which comprises a pulse generator and a shaping circuit. The pulse generator is configured to generate IRE pulses of a prespecified shape and repetition rate. The shaping circuit is configured to convert some of the IRE pulses into pacing pulses of a prespecified frequency and amplitude, to generate an output signal comprising ones of the IRE pulses interleaved with ones of the pacing pulses, and to output the output signal to a probe in a heart of a patient for applying the output signal to cardiac tissue. A processor my vary the output waveform to apply only pacing pulses, only IRE pulses, or M IRE pacing pulses and N IRE pulses RFA interleaved with N≥1. The catheter is configured for insertion into a heart of a patient and applying the output signal to heart tissue.

Other properties of the sequence can be configured through a processor that controls the generator, for example, IRE pulse shape and repetition rate, as well as pacing parameters such as pacing frequency. For example, for IRE the generator is able to generate biphasic pulses with peak to peak voltage of up to 4 kV, and at typical pulse-widths on the order of μSec. For pacing, the generator is able to generate pulses with peak voltage of up to few volts at a range of a few hundred cycles per minute.

Typically, the processor is programmed in software containing a particular algorithm that enables the processor to conduct each of the processor-related steps and functions outlined above.

The disclosed combined pacing and IRE technique may improve the clinical outcome of an invasive treatment of arrhythmia while at the same time decrease the work load experienced by the physician performing the procedure.

System Description

FIG. 1 is a schematic, pictorial illustration of a combined cardiac pacing and irreversible electroporation (IRE) system 20, in accordance with an exemplary embodiment of the present invention. System 20 may be configured to stimulate and analyze substantially any electrophysiological (EP) parameter or combination of such parameters. To this end, a console 46 of system 20 comprises a combined pacing/IRE pulse generator 33 that generates and applies interweaved pacing/IRE waveforms via a probe 24 to cardiac tissue in a heart 34 of a patient 26.

In the description herein, by way of example, the signals analyzed are assumed to be intra-cardiac and/or extra-cardiac (body surface) ECG potential-time relationships. In order to fully characterize such relationships, the signals at various locations need to be referenced in time to each other, such as is done, for example, while generating a local activation time (LAT) map. The time referencing is accomplished by measurements done relative to a reference time (e.g., instance), such as the beginning of each QRS complex of an ECG reference signal (i.e., the beginning of every heartbeat). A method for generating an LAT map is described in U.S. Pat. No. 9,050,011, cited above.

In the following description, system 20 stimulates (i.e., paces) heart 34 using a pacing and IRE probe 24. System 20 measures resulting electrical activity of a heart 34, using probe 24 itself and/or using an additional probe 14. A distal end 32 of probe 24 is assumed to have electrodes 22. The measured signals are used for, among other usages, creating an LAT map of at least a portion of the wall tissue of heart 34.

Typically, probe 24 comprises a mapping catheter which is inserted into the body of patient 26 during a mapping procedure performed by a physician 28 using system 20. As seen in inset 25, the procedure embodied in FIG. 1 uses an M1-M2 bipolar electrode pair configuration of probe 24 for pacing (i.e., for EP stimulation) and for IRE treatment of the tissue site found as arrhythmogenic using combined pacing and IRE pulse generator 33. In an exemplary embodiment, the catheter is further configured to acquire intracardiac electrophysiological signals.

During the procedure, patient 26 is assumed to be attached to a grounding electrode (i.e., ground patch) 23. In addition, electrodes 29 are assumed to be attached to the skin of patient 26, in the region of heart 34.

System 20 is controlled by a system processor 40, comprising a processing unit 42 communicating with a memory 44. In some exemplary embodiments, memory 44, which is included in system processor 40, stores an EP map 62 of at least a portion of wall tissue of heart 34 of patient 26. Processor 40 is typically mounted in console 46, which comprises (a) a patient interface unit 43 to which all the catheters connect, and (b) a workstation having operating controls 38, typically including a pointing device 39 such as a mouse or trackball used by physician 28 to interact with the processor.

Figure 3:
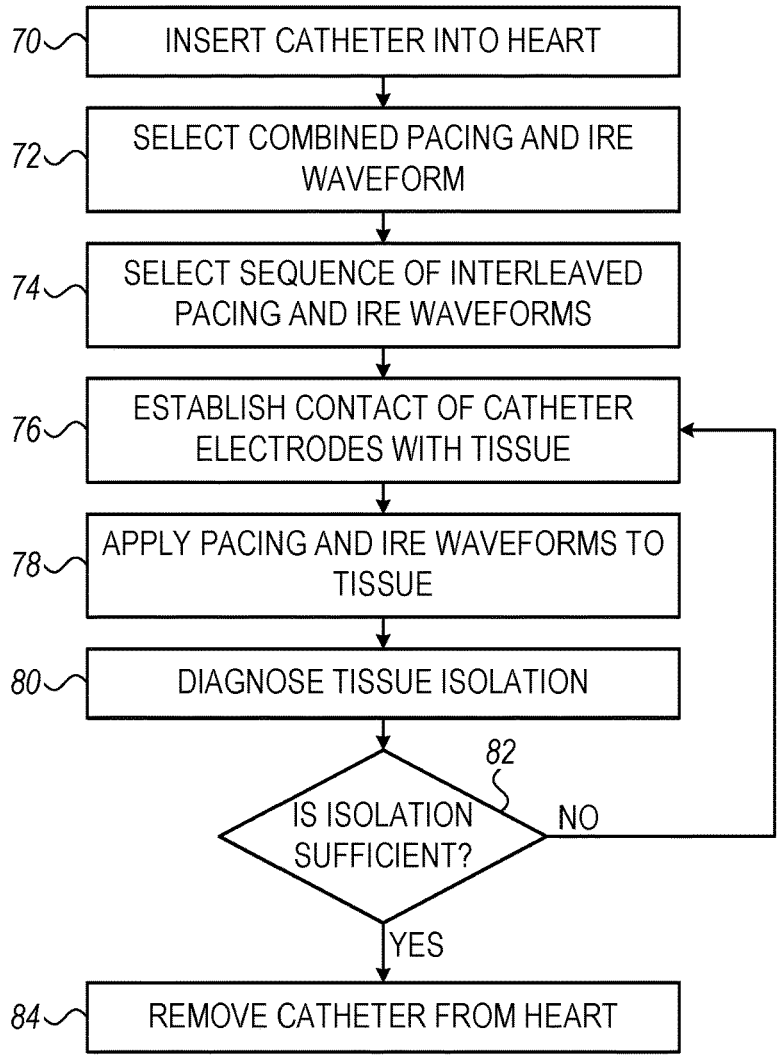
FIG. 3 is a flow chart that schematically illustrates a method of combined cardiac pacing and irreversible electroporation (IRE) using the system of FIG. 1, in accordance with an exemplary embodiment of the present invention.

Processor 40 (specifically processing unit 42) runs software comprising a probe tracker module 30, an ECG module 36 comprising an arrhythmia analysis module, and a graphical user interface (GUI) 35, to operate system 20 and/or to graphically analyze and present results (using EP map 62 stored in memory 44) from the disclosed heart pacing and IRE treatment workflow described in FIG. 3 so as, for example, to identify sources of an arrhythmia and to treat them with IRE.

In an exemplary embodiment, ECG module 36 is coupled to receive electrical signals from electrodes 22 and electrodes 29. The module is configured to analyze the electrical signals and may present the results of the analysis in a standard ECG format, typically a graphical representation moving with time, on display 48.

Probe tracker module 30 typically tracks the location of distal end 32 of probe 24 within the heart of patient 26. The tracker module may use any method for probe location tracking known in the art. For example, module 30 may operate a magnetic-field based location tracking sub-system. (For simplicity, components of such sub-system are not shown in FIG. 1.)

Alternatively or additionally, tracker module 30 may track probe 24 by measuring impedances between electrode 23 and electrodes 22, as well as the impedances to other electrodes which may be located on the probe. (In this case electrodes 22 may provide both ECG and location tracking signals.) The Carto3® system produced by Biosense-Webster (Irvine, Calif.) uses both magnetic field location tracking and impedance measurements for location tracking.

Using tracker module 30, processor 40 is able to measure locations of distal end 32. In addition, using both tracker module 30 and ECG module 36, the processor is able to measure locations of the distal end, as well as LATs of electrical signals detected at these particular locations.

Results of the operations performed by processor 40 are presented to physician 28 on a display 48, which typically presents a graphic user interface to the physician, a visual representation of the ECG signals sensed by electrodes 22, and/or an image or map of heart 34 while it is being investigated. In an embodiment, GUI 35 presents to the physician an EP map updated with one or more locations on the map where an identified arrhythmia originated or through which it propagated. The software may be downloaded to processor 40 in electronic form, over a network, for example, or it may, alternatively or additionally, be provided and/or stored on non-transitory tangible media, such as magnetic, optical, or electronic memory.

Combined Generation of Cardiac Pacing and Irreversible Electroporation (IRE)

Figure 2:
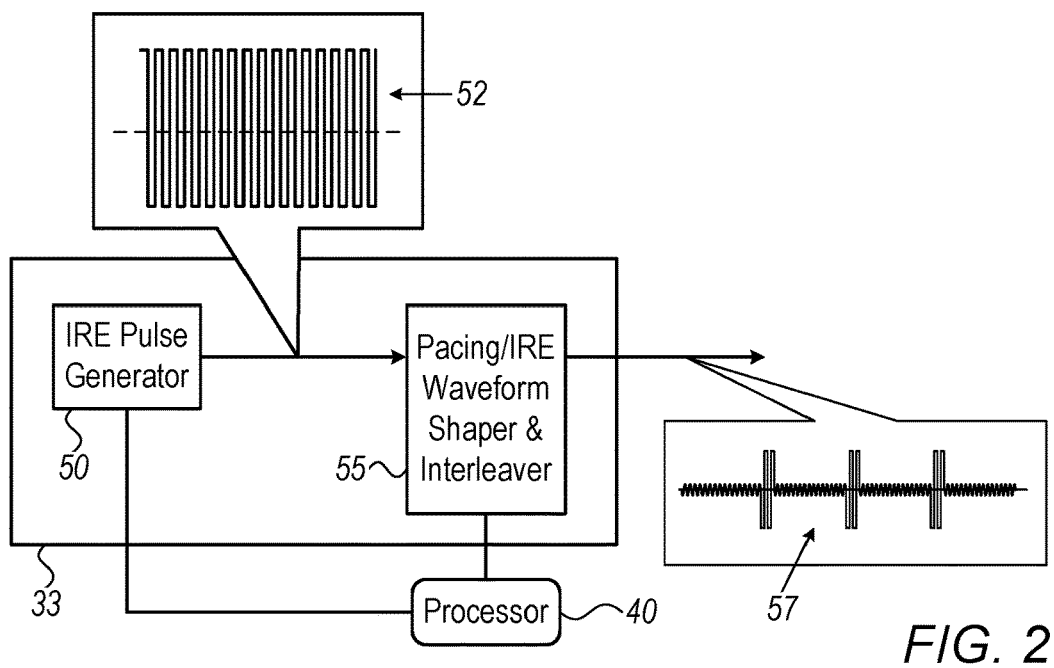
FIG. 2 is a schematic block diagram of the combined pacing and IRE pulse generator of the system of FIG. 1, in accordance with an exemplary embodiment of the present invention.

FIG. 2 is a schematic block diagram of the combined pacing and IRE pulse generator 33 of the system of FIG. 1, in accordance with an exemplary embodiment of the present invention. In the illustrated exemplary embodiment, generator 33 comprises an IRE pulse generator 50 and a pacing/IRE waveform shaper and interleaver 55, which are both configurable and controlled by processor 40.

As seen, IRE pulse generator 50 generates a sequence 52 of high-voltage biphasic pulses of a predefined waveform for IRE.

A shaping circuit 55, also called hereinafter "Pacing/IRE waveform shaper and interleaver 55," converts input sequence 52 into an interleaved pacing/IRE sequence 57 of output waveforms comprising, by way of example, M=2 IRE shape pulses interleaved with N=10 pacing pulses.

Pacing/IRE waveform shaper and pulse interleaver 55 comprises pulse shaper circuitry and waveform interleaving circuitry. The biphasic pulse shaper circuitry is configured to modify IRE pulses of sequence 52 to a shape and repetition rate required of pacing pulses. Typically, generator 33 includes electrical elements, such as a reinforced isolated amplifier, to convert the waveform voltage from the high-voltage domain of IRE pulses into a low-voltage domain of pacing pulses.

The pulse shaper may include an array of capacitors that may produce a different rise time and fall time of the pulses. Finally, the waveform interleaver comprises a switching circuitry to switch between IRE input and pacing pulses delivered to catheter 24.

The exemplary configurations illustrated in the FIG. 2 is chosen purely for the sake of conceptual clarity. In alternative embodiments, the disclosed techniques may use any other suitable pulse generation and shaping scheme.

Combined Cardiac Pacing and IRE Treatment

FIG. 3 is a flow chart that schematically illustrates a method of combined cardiac pacing and irreversible electroporation (IRE) using the system of FIG. 1 in accordance with an exemplary embodiment of the present invention.

The algorithm according to the presented exemplary embodiment carries out a process that begins with physician inserting catheter 24 into heart 34, at a catheter insertion step 70. Next, physician 28 selects, for example, a predefined protocol with a combined pacing/IRE waveform to be given to tissue, at protocol selection step 72. As noted above, physician 28 may select to start with pacing signals only, for example, to begin a preliminary diagnosis.

Assuming a preliminary diagnosis session has ended and physician 28 chooses to apply a mixture of pacing and IRE pulses, such as shown by waveform 57 of FIG. 2, physician 28 specifies an interleaved sequence of IRE/RFA waveforms, for example, as specified by the selected protocol, at an interleaved sequence selection step 74. For example, physician 30 may select an {M=15, N=3} sequence, as defined above.

Next, at catheter positioning step 76, physician 30 manipulates catheter 24 to establish contact between electrodes M1-M2 of catheter 24 and tissue, such as of an ostium of a pulmonary vein. Next, physician 28 applies the selected interleaved sequence of pacing/IRE pulses to tissue, at a pacing/IRE application step 78.

Immediately after treatment, at a post pacing/IRE application diagnostic step 80, using electrodes M1-M2 of catheter 24 as diagnostic electrodes, physician 28 acquires electrograms to check to what extent treatment step 78 achieved isolation. If, at a checking step 82, the physician finds that sufficient isolation was achieved, physician 30 then removes the catheter from the patient body, at a catheter retraction step 84. Otherwise, physician 28 may loop back to step 76 to reposition the catheter and continue the session.

Although the exemplary embodiments described herein mainly address cardiac applications, the methods and systems described herein can also be used in various other medical applications.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A cardiac pacing and irreversible electroporation (IRE) apparatus, comprising:
    a pulse generator, which is configured to generate IRE pulses of prespecified shape and repetition rate; and
    a shaping circuit, coupled to one or more processors, that comprises shaper circuitry configured to convert some of the IRE pulses into pacing pulses of prespecified frequency and amplitude by modifying the IRE pulses to a shape and repetition rate required of pacing pulses and waveform interleaving circuitry configured to switch between the IRE pulses and the converted pacing pulses and generate an interleaved output signal consisting of ones of the IRE pulses interleaved with ones of the converted pacing pulses at a specified interleaved sequence, and to output the output signal to a probe in a heart of a patient for applying the output signal to cardiac tissue and for performing substantially simultaneously and/or sequentially diagnostic pacing and IRE treatment of an arrhythmia at a given cardiac tissue location using the interleaved output signal.

2. The apparatus according to claim 1, and comprising a processor configured to:
    specify the shape and the repetition rate of the IRE pulses;
    specify the frequency and the amplitude of the pacing pulses; and
    specify the interleaved output signal, by specifying a number of the one or more IRE pulses and a number of the one or more pacing pulses.

3. The apparatus according to claim 1, wherein the shaping circuit is further configured to modify a prespecified shape of the IRE pulses.

4. The apparatus according to claim 1, wherein the shaping circuit is configured to interleave the IRE pulses with the pacing pulses in the output signal in accordance with a configurable protocol.

5. A method of applying cardiac pacing and irreversible electroporation (IRE) pulses, the method comprising:
    generating IRE pulses of prespecified shape and repetition rate;
    converting some of the IRE pulses into pacing pulses of prespecified frequency and amplitude by modifying the IRE pulses to a shape and repetition rate required of pacing pulses and waveform interleaving circuitry configured to switch between the IRE pulses and the converted pacing pulses and generating an interleaved output signal consisting of ones of the IRE pulses interleaved with ones of the pacing pulses at a specified interleaved sequence; and
    outputting the output signal to a probe in a heart of a patient for applying the output signal to cardiac tissue and for performing substantially simultaneously and/or sequentially diagnostic pacing and IRE treatment of an arrhythmia at a given cardiac tissue location using the interleaved output signal.

6. The method according to claim 5, and comprising, using a processor:
    specifying the shape and the repetition rate of the IRE pulses;
    specifying the frequency and the amplitude of the pacing pulses; and
    specifying the interleaved output signal, by specifying a number of the one or more IRE pulses and a number of the one or more periods of the RF signal.

7. The method according to claim 5, and comprising shaping the IRE pulses by modifying the prespecified shape of the IRE pulses.

8. The method according to claim 5, wherein interleaving the IRE pulses with the pacing pulses is performed in accordance with a configurable protocol.

9. A cardiac pacing and irreversible electroporation (IRE) apparatus, comprising:
    a pulse generator configured to generate IRE pulses of prespecified shape and repetition rate; and
    a shaping circuit configured to: i) convert some of the IRE pulses into pacing pulses of prespecified frequency and amplitude, ii) interleave ones of the IRE pulses with ones of the converted pacing pulses, iii) generate an output signal comprising one of pacing pulses, IRE pulses or converted pacing pulses interleaved with IRE pulses, and iv) output the output signal to a probe in a heart of a patient for applying the output signal to cardiac tissue.

10. The apparatus according to claim 9, and comprising a processor configured to:
    specify the shape and the repetition rate of the IRE pulses;
    specify the frequency and the amplitude of the pacing pulses; and
    specify the interleaved output signal, by specifying a number of the one or more IRE pulses and a number of the one or more pacing pulses.

11. The apparatus according to claim 9, wherein the shaping circuit is further configured to modify a prespecified shape of the IRE pulses.

12. The apparatus according to claim 9, wherein the shaping circuit is configured to interleave the IRE pulses with the pacing pulses in accordance with a configurable protocol.

* * * * *